US011874282B2

(12) United States Patent
Hund et al.

(10) Patent No.: US 11,874,282 B2
(45) Date of Patent: Jan. 16, 2024

(54) IGFBP-7 AS A MARKER OF PREECLAMPSIA

(71) Applicant: Roche Diagnostics Operations, Inc., Indianapolis, IN (US)

(72) Inventors: Martin Hund, Horw (CH); Edelgard Anna Kaiser, Huenenberg See (CH); Ursula-Henrike Wienhues-Thelen, Krailling (DE); Dirk Block, Bichl (DE); Johann Karl, Peissenberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 16/110,687

(22) Filed: Aug. 23, 2018

(65) Prior Publication Data

US 2018/0364248 A1    Dec. 20, 2018

Related U.S. Application Data

(63) Continuation of application No. PCT/EP2017/054484, filed on Feb. 27, 2017.

(30) Foreign Application Priority Data

Feb. 29, 2016   (EP) .................................... 16157794

(51) Int. Cl.
  *G01N 31/00*   (2006.01)
  *G01N 33/53*   (2006.01)
  *G01N 33/68*   (2006.01)
  *G16B 99/00*   (2019.01)
  *G16B 20/00*   (2019.01)
  *G16B 25/10*   (2019.01)

(52) U.S. Cl.
  CPC ....... *G01N 33/689* (2013.01); *G01N 33/6893* (2013.01); *G16B 20/00* (2019.02); *G16B 25/10* (2019.02); *G16B 99/00* (2019.02); *G01N 2333/4703* (2013.01); *G01N 2333/4745* (2013.01); *G01N 2800/368* (2013.01); *G01N 2800/52* (2013.01); *G01N 2800/60* (2013.01)

(58) Field of Classification Search
  None
  See application file for complete search history.

(56) References Cited

U.S. PATENT DOCUMENTS

| 4,016,043 A | 4/1977 | Schuurs et al. |
| 4,018,653 A | 4/1977 | Mennen |
| 4,424,279 A | 1/1984 | Bohn et al. |
| 5,712,103 A | 1/1998 | Leavitt et al. |
| 10,996,229 B2 * | 5/2021 | Wienhues-Thelen ........ G01N 33/6893 |
| 2015/0099655 A1 * | 4/2015 | Butte ..................... G16B 25/10 506/18 |

FOREIGN PATENT DOCUMENTS

| EP | 2666872 A1 | 11/2013 | |
| WO | 2004/008946 A2 | 1/2004 | |
| WO | 2007059065 A2 | 5/2007 | |
| WO | 2008/089994 A1 | 7/2008 | |
| WO | 2010/043037 A1 | 4/2010 | |
| WO | 2012/107419 A1 | 8/2012 | |
| WO | 2013068475 A1 | 5/2013 | |
| WO | 2013169751 A1 | 11/2013 | |
| WO | 2014/001244 A1 | 1/2014 | |
| WO | 2014/086833 A1 | 6/2014 | |
| WO | 2015/110624 A1 | 7/2015 | |
| WO | WO-2015110624 A1 * | 7/2015 | ......... G01N 33/6863 |
| WO | 2015/144767 A1 | 10/2015 | |
| WO | 2016/019176 A1 | 2/2016 | |
| WO | WO-2016019176 A1 * | 2/2016 | ............. G01N 33/50 |
| WO | 2016034767 A1 | 3/2016 | |
| WO | 2017148854 A1 | 9/2017 | |

OTHER PUBLICATIONS

Mills et al. JAMA. 1999;282:356-362 (Year: 1999).*
Acro Biosystems, IGFBP-7 Protein—background copyright 2017 (Year: 2017).*
Liu et al. (BMC Medicine, 2013, 11:236, pp. 1-12) (Year: 2013).*
International Search Report dated Mar. 31, 2017, in Application No. PCT/EP2017/054484, 3 pp.
ACOG Practice Bulletin No. 33, Clinical Management Guidelines for Obstetrician-Gynecologiests, Obstetrics & Gynecology, 2002, pp. 159-167, vol. 99.
Antenatal care for uncomplicated pregnancies, National Institute for Health and Care Excellence, 2008, 45 pp., CG62.
Berg, Cynthia J. et al., "Pregnancy-Related Mortality in the United States, 1998 to 2005," Obstetrics & Gynecology, 2010, pp. 1302-1309, vol. 116, No. 6.
Bouzari, Z. et al., Does proteinura in preeclampsia have enough value to predict pregnancy outcome?, Clinical and Experimental Obstetrics and Gynecology, 2014, pp. 163-168, vol. 41, No. 2.
Brown, Mark A. et al., The Classification and Diagnosis of the Hypertensive Disorders of Pregnancy: Statement from the International Society for the Study of Hypertension in Pregnancy (ISSHP), Hypertension in Pregnancy, 2001, pp. x-xiv, vol. 20, No. 1.

(Continued)

*Primary Examiner* — Lisa V Cook
(74) *Attorney, Agent, or Firm* — Stinson LLP

(57) ABSTRACT

The present disclosure relates to a method for diagnosing preeclampsia or a preeclampsia-related condition in a pregnant subject. The method is based on the measurement of the amount of the biomarker IGFBP-7 (Insulin-like Growth Factor Binding Protein 7) in a sample from the subject and on the comparison of the measured amount to a reference. Also disclosed are methods for assessing the severity of preeclampsia or a preeclampsia-related condition and methods for monitoring a preeclampsia or a preeclampsia-related condition in a pregnant subject. The present disclosure further relates to the use of the biomarker IGFBP-7 or of an agent that specifically binds to IGFBP-7 in a sample from a pregnant subject for diagnosing, for monitoring or for assessing the severity of preeclampsia or a preeclampsia-related condition. Finally, the present disclosure relates to a device or kit adapted to carry out the method of the present invention.

13 Claims, 10 Drawing Sheets

(56) References Cited

OTHER PUBLICATIONS

Diagnostics Assessment Programme PIGF-based testing to help diagnose suspected pre-eclampsia (Triage PIGF test, Elecsys immunoassay sFlt-1/PIGF ratio, DELFIA Xpress PIGF 1-2-3 test, and BRAHMS sFlt-1 Kryptor/BRAHMS PIGF plus Kryptor PE ratio), National Institute for Health and Care Excellence, 2015, 26 pp.

Duley, Lelia, "The Global Impact of Pre-eclampsia and Eclampsia," Seminars in Perinatology, 2009, pp. 130-137, vol. 33.

Ghulmiyyah, Labib and Sibai, Baha, Maternal Mortality From Preeclampsia/Eclampsia, Seminars in Perinatology, 2012, pp. 56-59, vol. 36.

Hagmann, Henning et al., The Promise of Angiogenic Markers for the Early Diagnosis and Prediction of Preeclampsia, Clinical Chemistry, 2012, 9 pages, vol. 58, No. 5.

Hypertension in Pregnancy Report of the American College of Obstetricians and Gynecologists' Task Force on Hypertension in Pregnancy, Obstetrics & Gynecology, 2013, pp. 1122-1131, vol. 122.

Hypertension in pregnancy: diagnosis and management, National Institute for Health and Care Excellence, 2011, 49 pp., CG107.

Kendall, Richard L. et al., Identification of a Natural Soluble Form of the Vascular Endothelial Growth Factor Receptor, FLT-1, and its Heterodimerization with KDR, Biochemical and Biophysical Research Communications, 1996, pp. 324-328, vol. 226.

Maglione, Domenico et al., Two alternative mRNAs coding for the angiogenic factor, placenta growth factor (PIGF), are transcribed from a single gene of chromosome 14, Oncogene, 1993, pp. 2333-2339, vol. 8.

Meersch, Melanie et al., Urinary TIMP-2 and IGFBP7 as Early Biomarkers of Acute Kidney Injury and Renal Recovery following Cardiac Surgery, PLOS One, 2014, e93460, 9 pp., vol. 9, No. 3.

Ono, Yasuhiro et al., Expression of prostacyclin-stimulating factor, a novel protein, in tissues of Wistar rats and in cultured cells, Biochemical and Biophysical Research Communications, 1994, pp. 1490-1496, vol. 202, No. 3.

Report of the National High Blood Pressure Education Program Working Group on High Blood Pressure in Pregnancy, American Journal of Obstetrics and Gynecology, 2000, pp. S1-S22, vol. 183, No. 1.

Richter, Mark M., Electrochemiluminescence (ECL), Chemical Reviews, 2004, pp. 3003-3036, vol. 104.

Sunderji, Shiraz et al., "Automated assays for sVEGF R1 and PIGF as an aid in the diagnosis of preterm preeclampsia: a prospective clinical study," American Journal of Obstetrics & Gynecology, 2010, pp. 40.e1-40.e7, vol. 202.

Young, Brett et al., "The use of angiogenic biomarkers to differentiate non-HELLP related thrombocytopenia from HELLP syndrome," The Journal of Maternal-Fetal and Neonatal Medicine, 2010, pp. 366-370, vol. 23, No. 5.

Zweig, Mark H. and Campbell, Gregory, Receiver-Operating Characteristic (ROC) Plots: A Fundamental Evaluation Tool in Clinical Medicine, Clinical Chemistry, 1993, pp. 561-577, vol. 39, No. 4.

Liao, S. Maternal Serum IGF-1, IGFBP-1 and 3, and placental growth hormone at 20 weeks' gestation in pregnancies complicated by preeclampsia, Pregnancy Hypertension, Jul. 27, 2017, vol. 10, pp. 149-154.

NICE (2011) NICE clinical guideline 107: Hypertension in Pregnancy; 295-pages.

Kusanovic 2009, A Prospective Cohort Study of the Value of Maternal Plasma Concentrations of Angiogenic and Anti-angiogenic Factors in Early Pregnancy and Midtrimester in the Identification of Patients Destined to Develop Preeclampsia; J of Maternal-Fetal and Neonatal Medicine 22(11): pp. 1021-1038.

Ohkuchi 2011, Threshold of Soluble Fms-Like Tyrosine Kinase 1/Placental Growth Factor Ratio for the Imminent Onset of Preeclampsia; Hypertension vol. 58: pp. 859-866.

Stepan 2007, Predictive Value of Maternal Angiogenic Factors in Second Trimester Pregnancies With Abnormal Uterine PerfusionHypertension, vol. 49: pp. 818-824.

Stepan 2008, Circulatory soluble endoglin and its predictive value for preeclampsia in second-trimester pregnancies with abnormal uterine perfusion; Am J Obstet Gynecol vol. 198: pp. 175.e1-1.

Thangaratinam et al. Estimation of proteinuria as a predictor of complications of pre-eclampsia: a systematic review. BMC Medicine 2009;7:10.

Zhang et al. Prediction of adverse outcomes by common definitions of hypertension in pregnancy. Obstet Gynecol 2001; 97:261-7.

Jisook Park et al.: "Discovery of the serum biomarker proteins in severe preeclampsia by proteomic analysis", Experimental and Molecular Medicine, vol. 43, No. 7, Jan. 1, 2011, p. 427.

Zhen-Kun Liu et al.: „A Novel Role of IGFBP7 in Mouse Uterus: Regulating Uterine Receptivity through Th1/Th2 Lymphocyte Balance and Decidualization, PLOS One, vol. 7, No. 9, Sep. 17, 2012, p. e45224.

\* cited by examiner

IGFBP-7 AS A MARKER OF PREECLAMPSIA

CROSS REFERENCE TO RELATED APPLICATIONS

This application is a continuation of International Application No. PCT/2017/054484 filed Feb. 27, 2017, which claims priority to European Application No. 16157794.5 filed Feb. 29, 2016, the disclosures of which are hereby incorporated by reference in their entirety.

SUMMARY OF THE INVENTION

The present invention relates to a method for diagnosing preeclampsia or a preeclampsia-related condition in a pregnant subject. Said method is based on the measurement of the amount of the biomarker IGFBP-7 (Insulin-like Growth Factor Binding Protein 7) in a sample from the subject and on the comparison of the measured amount to a reference. Also encompassed by the present invention are methods for assessing the severity of preeclampsia or a preeclampsia-related condition and methods for monitoring a preeclampsia or a preeclampsia-related condition in a pregnant subject. The present invention further relates to the use of the biomarker IGFBP-7 or of an agent that specifically binds to IGFBP-7 in a sample from a pregnant subject for diagnosing, for monitoring or for assessing the severity of preeclampsia or a preeclampsia-related condition. Finally, the present invention relates to a device adapted to carry out the method of the present invention.

BACKGROUND OF THE INVENTION

Hypertensive disorders represent the most common medical complication of pregnancy, affecting approximately 6 to 8 percent of gestations (Report of the National High Blood Pressure Education Program Working Group on High Blood Pressure in Pregnancy. Am J Obstet Gynecol. 2000; 183(1): S1-522).

Pregnancy complications are, on one hand, associated with pregnancy related mortality of the pregnant woman and, on the other hand, also associated with increased morbidity and mortality of the newborn. In pregnant women above the age of 39 years, maternal mortality at a rate of 14.5 per 100,000 live births is even more frequent. Besides hypertensive disorders, hemorrhage, thrombotic pulmonary embolism, infections, cardiomyopathy as well as cardiovascular and non-cardiovascular conditions may cause complications and increase mortality (Berg 2010, Obstetrics and Gynecology: 116: 1302-1309).

Hypertensive disorders of pregnancy can be classified as 1) preeclampsia, 2) chronic hypertension (of any cause), 3) chronic hypertension with superimposed preeclampsia, and 4) gestational hypertension (ACOG Task Force on Hypertension in Pregnancy. Obstet Gynecol 2013; 122:1122-31). The clinical management generally includes blood pressure control in the case of preeclampsia and chronic hypertension, seizure prevention in the case of severe hypertension or severe hypertension with eclamptic fit, earlier delivery—34 weeks versus 37 weeks—in the case of chronic hypertension with superimposed preeclampsia and intensive postpartum surveillance in the case of gestational hypertension (NICE (2011) NICE clinical guideline 107: Hypertension in Pregnancy).

Preeclampsia is the most important hypertensive disorder during pregnancy associated with mortality and morbidity for mother and fetus/newborn. (Duley 2009, Semin Perinatol: 33: 130-37).

Preeclampsia is generally defined as pregnancy associated or induced hypertension. It is characterized by hypertension and proteinuria. Details are also found in the standard text books of medicine and the Guidelines of the various clinical societies, e.g. Brown MA,: The classification and diagnosis of the hypertensive disorders of pregnancy: statement from the International Society for the Study of Hypertension in Pregnancy (ISSHP). Hypertens Pregnancy 2001, 20:IX-XIV or ACOG Practice Bulletin, Clinical Management Guidelines for Obstetrician—Gynecologists, no.: 33, January 2002 or DGGG. S 1-Leitlinie: Diagnostik und Therapie hypertensiver Schwanger-schaftserkrankungen der Deutschen Gesellschaft fur Gynakologie und Geburtshilfe, AWMF on-line, AWMF Register Nummer 015/018, Klasse 51 orNICE (2011) NICE clinical guideline 107: Hypertension in Pregnancy).

Currently there are no cures for preeclampsia other than delivery. Preeclampsia can vary in severity from mild to life threatening. A mild form of preeclampsia can be treated with bed rest and frequent monitoring. For moderate to severe cases, hospitalization is recommended and blood pressure medication or anticonvulsant medications to prevent seizures are prescribed. If the condition becomes life-threatening to the mother or the baby, the pregnancy is terminated and the baby is delivered pre-term.

In addition to preeclampsia, there are further preeclampsia-related adverse outcomes such as the HELLP syndrome and eclampsia. HELLP syndrome is a life-threatening obstetric complication and involves hemolytic anemia, elevated liver function tests (LFTs), and low platelet count. HELLP usually begins during the third trimester. Unexpectedness, suddenness, and fulminant course of this syndrome are essential. Eclampsia is commonly defined as new onset of grand mal seizure activity and/or unexplained coma during pregnancy in a woman with signs or symptoms of preeclampsia. Mortality from eclampsia ranges from approximately 1% in the developed world, to as high as 15% in the developing world (Ghulmiyyah L, Sibai B M. Maternal Mortality from Preeclampsia/Eclampsia. Semin Perinatol 2012; 36:56-59.)

According to current guidelines, diagnosis of preeclampsia is based on the new onset of hypertension and proteinuria after gestational week 20 in pregnant women. A blood pressure greater than or equal to 140 mmHg systolic or greater than or equal to 90 mmHg dia-stolic on two occasions at least 4 hours apart after 20 weeks of gestation in a woman with a previously normal blood pressure is considered hypertensive. The reliable detection of significant proteinuria is most important in women with new-onset hypertension during pregnancy because it distinguishes between those pregnancies with preeclampsia and those with gestational hypertension and this sets the scene for future monitoring and management. Significant proteinuria is defined internationally as the urinary excretion of more than 300 mg protein in a 24-hour period, and this is included in definitions of preeclampsia (NICE (2011) NICE clinical guideline 107: Hypertension in Pregnancy).

Determination of proteinuria can be realized by 24-hour urine collection, protein/creatinine ratio calculation or dipstick readings. (Executive Summary: Hypertension in Pregnancy, American College of Obstetricians and Gynecologist, Obstet Gynecol 2013; 122:1122-31).

Determination of proteinuria is often done with urine protein dipsticks because the method allows for rapid measurement of proteinuria. However, it is often fraught with incorrect results and thus a quite inaccurate method to determine kidney dysfunction. Moreover, due to the variability of qualitative determination, this method is discouraged for diagnostic use and should only be used if other quantitative methods are not available (ACOG Task Force, 2013). Especially amongst women with hypertensive problems, there are high rates of incorrect urinary dipstick results. Of concern, up to 66% of hypertensive women with a negative urinary dipstick were found to have significant proteinuria." (North R. Classification and diagnosis of preeclampsia. In Preeclampsia: Etiology and Clinical Practice, pages 250-251).

More accurate methods to determine protein in urine are 24 hour urine measurements (generally greater or equal to 300 mg per 24 h urine collection for diagnosis of preeclampsia) or the calculation of protein-creatinine ratio (generally greater than or equal to 0.3, each measured as mg/dl). However, these methods also have certain drawbacks. For example, they are more time-consuming and under certain conditions also error-prone. Bouzari et al. found that proteinuria (determined by 24 h urine measurement) in patients with preeclampsia was associated with adverse outcome in pregnancy. However, it was not an adequate predictor of adverse outcome in preeclampsia (Bouzari Z, Javadiankutenai M, Darzi A, Barat S.: Clin Exp Obstet Gynecol. 2014; 41(2):163-8).

Recently, several angiogenic and anti-angiogenic proteins have been suggested as diagnostic or prognostic factors for preeclampsia. Known diagnostic or prognostic methods include the determination of soluble fms-like tyrosine kinase-1 (sFlt-1), Endoglin or Placental Growth Factor (PlGF), as well as the determination of ratios between these factors (WO 2004/008946, Young 2010, J. Matern, Fetal Neonatal Med 23(5): 20 366-370; Hagmann 2012, Clinical Chemistry 58(5): 1-9). In addition, the ratio of sFlt-1/PlGF or Endoglin/PlGF can be used to rule-out the onset of preeclampsia within a certain time window (WO 2014/001244).

However, determination of proteinuria after gestational week 20 in pregnant women remains a standard diagnostic factor for preeclampsia. Therefore, a reliable, sensitive and quantitative biomarker to indicate kidney dysfunction during pregnancy would be highly desirable (NICE (2015) PlGF-based testing to help diagnose suspected pre-eclampsia. Diagnostic assessment programme).

IGFBP-7 (Insulin-like growth factor binding protein 7) is a 30-kDa modular glycoprotein known to be secreted by endothelial cells, vascular smooth muscle cells, fibroblasts, and epithelial cells (Ono, Y., et al., Biochem Biophys Res Comm 202 (1994) 1490-1496).

WO 2008/089994 discloses the use of IGFBP-7 in the assessment of heart failure

Urinary IGFBP-7 in combination with TIMP-2 (marketed as Nephrocheck®) has been shown to be a sensitive and specific biomarker to predict acute kidney injury (AKI) early after cardiac surgery and to predict renal recovery (Meersch et al. PLoS One. 2014 Mar. 27; 9(3)).

EP 2 666 872 A1 discloses various markers for the diagnosis and prognosis of renal injury and renal failure including the marker IGFBP-7.

IGFBP-7 has also been described as a biomarker for cancer and the use of anti-IGFBP-7 antibodies was suggested as diagnostic tool for detecting neoplastic diseases including tumor angiogenesis (WO 2010/043037).

With respect to the drawbacks of the currently used methods to determine proteinuria in women with suspected preeclampsia, there is a strong need to develop new methods to indicate proteinuria in women with suspected preeclampsia and pregnant women in general to screen for preeclampsia.

Thus, a reliable and sensitive biomarker to indicate preeclampsia or conditions associated with preeclampsia (such as proteinuria) in pregnancy is required.

DETAILED DESCRIPTION OF THE INVENTION

Figure 1:
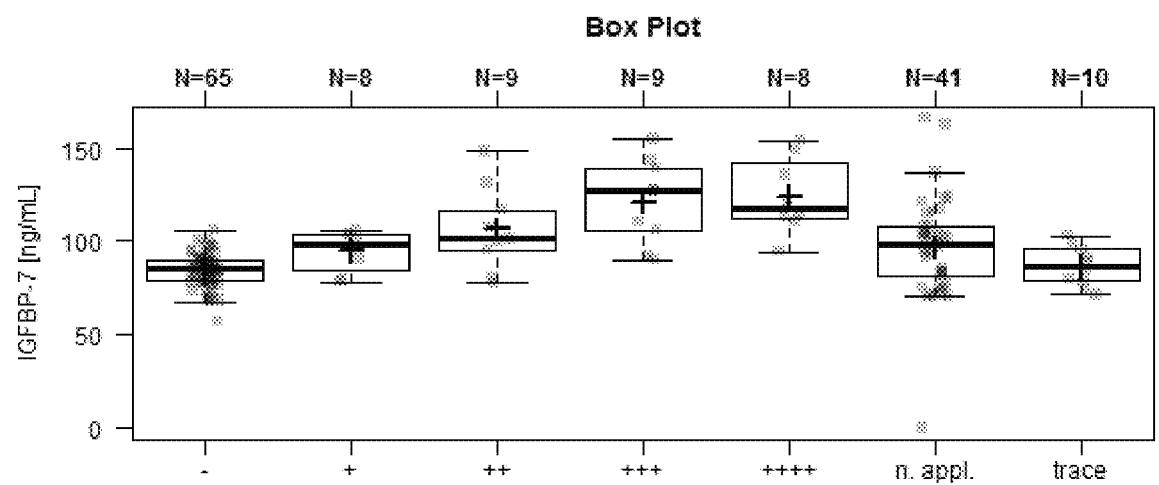
FIG. 1: Boxplots for IGFBP-7 divided by different dipstick measurements. The IGFBP-7 serum levels are increased with increasing amounts of protein in urine detected by protein dipstick results in pregnant women.

The technical problem underlying the present invention can be seen as the provision of means and methods for complying with the aforementioned needs. The technical problem is solved by the embodiments characterized in the claims and herein below.

Surprisingly, it was found in the context of the studies of the present invention that the measurement of the amount of IGFBP-7 in a sample from a pregnant subject allows for a fast and reliable diagnosis of preeclampsia or preeclampsia-related conditions (such as eclampsia, HELLP syndrome or proteinuria). For example, the identification of proteinuria in women with suspected preeclampsia was more accurately than with currently used methods such as the dipstick protein test.

Accordingly, the present invention relates to a method for diagnosing preeclampsia or a preeclampsia-related condition in a subject, said method comprising the steps of
(a) measuring the amount of IGFBP-7 (Insulin-like Growth Factor Binding Protein 7) in a sample from the subject, and
(b) comparing the measured amount of the biomarker to a reference.

In an embodiment of the present invention, preeclampsia or a preeclampsia-related condition is diagnosed by carrying out the further step (c) of diagnosing preeclampsia or a preeclampsia-related condition. Said diagnosis shall be based on the result of the comparison carried out in step (b).

The method of the present invention, preferably, is an in vitro method. Moreover, it may comprise steps in addition to those explicitly mentioned above. For example, further steps may relate to sample pre-treatments or evaluation of the results obtained by the method. The method of the present invention may be also used for monitoring, confirmation, and sub-classification of the subject. The method may be carried out manually or assisted by automation. Preferably, step (a), (b) and/or (c) may in total or in part be assisted by automation, e.g., by a suitable robotic and sensory equipment for the determination in step (a) or a computer-implemented calculation in step (b).

The term "diagnosing" as used herein means assessing whether a subject as referred to in accordance wih the method of the present invention suffers from preeclampsia or a preeclampsia-related condition, or not. As will be understood by those skilled in the art, such an assessment is usually not intended to be correct for all (i.e. 100%) of the subjects to be identified. The term, however, requires that a statistically significant portion of subjects can be correctly assessed (e.g., a cohort in a cohort study). Whether a portion is statistically significant can be determined without further ado by the person skilled in the art using various well-known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. More preferably, at least 60%, at least 70%, at least 80% or at least 90% of the subjects of a population can be properly assessed by the method of the present invention.

In accordance with the present invention, preeclampsia or a preeclampsia-related condition in a subject shall be diagnosed. Preeclampsia or preeclampsia-related conditions are well-known in the art. In an embodiment, the preeclampsia-related condition is selected from eclampsia, HELLP syndrome and proteinuria.

The term "preeclampsia" as used herein refers to a medical condition which is characterized by hypertension and proteinuria. Preeclampsia occurs in pregnant female subjects and the hypertension in that context is also referred to as pregnancy-induced hypertension. Preferably, the pregnancy-induced hypertension is identified to be present in a subject by two blood pressure measurements of 140 mmHg (systolic) and/or 90 mmHg (diastolic) or more, wherein said two measurements have been made at least 6 hours apart. Proteinuria can be identified to be present by 300 mg protein or more in a 24-hour urine sample. Also, proteinuria can be identified by protein dipstick analysis (if ≥2+), if ≥30 mg/dL protein are present in a spot urine sample, or by a protein/creatinine ratio of ≥30 mg protein/mmol creatinine in spot urine.

Preeclampsia in accordance with the present invention can be a mild form or severe form preeclampsia. The terms "mild preeclampsia" and "severe preeclampsia" are well-known in the art. The term "mild preeclampsia" preferably refers to the presence proteinuria and of hypertension (in particular of a blood pressure ≥140/90 mmHg) on 2 occasions, at least 6 hours apart, but without evidence of end-organ damage in a woman who was normotensive before week 20 of gestation. The term "severe preeclampsia" refers to preeclampsia with at least one of the following symptoms, systolic blood pressure of 160 mmHg or higher or diastolic blood pressure of 110 mmHg or higher on 2 occasions at least 6 hours apart, proteinuria of more than 5 g in a 24-hour collection or more than 3+ on 2 random urine samples collected at least 4 hours apart, oliguria (in particular of less than 400 mL urine in 24 hours), persistent headaches, epigastric pain and/or impaired liver function and thrombocytopenia.

The studies carried out in the context of the present invention show that both early-onset and late-onset preeclampsia can be reliably diagnosed. Early-onset preeclampsia occurs between about week 20 and about week 34 of gestation. Thus, it is envisaged to obtain the sample between about week 20 and about week 34 of gestation for the diagnosis of early-onset preeclampsia. Late-onset preeclampsia occurs after week 34 of gestation. Thus, it is envisaged to obtain the sample after week 34 of gestation for the diagnosis of late-onset preeclampsia.

Preeclampsia may progress to eclampsia, a life-threatening disorder characterized by the appearance of tonic-clonic seizures or coma conditions. Symptoms associated with severe preeclampsia are oliguria of less than 500 ml within 24 hours, cerebral or visual disturbance, pulmonary edema or cyanosis, epigastric- or right upper quadrant-pain, impaired liver function, thrombocytopenia.

The term "HELLP syndrome" is well-known in the art. The HELLP syndrome is a life-threatening obstetric complication usually considered complication of preeclampsia. The HELLP syndrome usually occurs during the later stages of pregnancy. The HELLP syndrome is associated with a high risk of adverse outcomes such as renal failure, subcapsular hepatic hematoma, recurrent preeclampsia, or even death. "HELLP" is an abbreviation of the three main features of the syndrome: Hemolysis, Elevated Liver enzymes, and Low Platelet count. HELLP syndrome can be difficult to diagnose due to the variability of symptoms among patients (frequently patients have no symptoms other than general abdominal pain), and early diagnosis is key in reducing morbidity. If not treated in a timely manner, patients can become critically ill or die due to liver rupture/hemorrhage or cerebral edema. In a patient with possible HELLP syndrome, a batch of blood tests is performed: a full blood count, a coagulation panel, liver enzymes, electrolytes, and renal function studies. Often, fibrin degradation product (FDP) levels are determined, which can be elevated. Lactate dehydrogenase is a marker of hemolysis and is elevated (>600 U/liter).

In a preferred embodiment of the present invention proteinuria is diagnosed.

The term "proteinuria" refers to a condition in which excess protein is present in the urine of a subject. Preferably, a subject suffers from proteinuria if the amount of urinary protein exceeds 0.3 g in a 24-hour urine collection. Also preferably, a subject suffers from proteinuria if the protein amount is equal to or larger than 30 mg/dL in a spot urine sample, in particular at least two sport urine samples obtained from the subject at least 6 hours apart.

The "subject" as referred to herein is, preferably, a mammal. Mammals include, but are not limited to, domesticated animals (e.g., cows, sheep, cats, dogs, and horses), primates (e.g., humans and non-human primates such as monkeys), rabbits, and rodents (e.g., mice and rats). Preferably, the subject is a human subject. In one embodiment the subject according to the present invention shall be pregnant. In this embodiment, the subject shall be female. In an embodiment, the pregnant subject is between about week 20 and about week 40 of gestation, in particular, between about week 24 and about week 40 of gestation.

In an embodiment, the subject (such as the pregnant subject) to be tested suffers from hypertension, suffers from preeclampsia, eclampsia, HELLP syndrome and/or proteinuria, or the subject be tested may be an at risk person for preeclampsia or a preeclampsia-related condition.

In an embodiment, the subject to be tested suffers from hypertension. Hypertension is defined in this context as blood pressure of 140 mmHg (systolic) and/or 90 mmHg (diastolic) or more at two independent measurements, wherein said two measurements have been made at least 6 hours apart. In an embodiment, the hypertension is new-onset hypertension. Thus, it is envisaged that the pregnant subject shall not have suffered from hypertension before pregnancy.

In one embodiment, the diagnosis of preeclampsia in a pregnant subject, e.g. at risk for preeclampsia or suspected to suffer from preeclampsia is based on the measurement of both IGFBP-7 and blood pressure. Presence of both new-onset hypertension as well as new-onset of an increased amount of IGFBP-7 indicates preeclampsia. According to the updated ACOG guidelines preeclampsia is also defined as new onset of hypertension and new onset of renal insufficiency (ACOG Task Force on Hypertension in Pregnancy. Obstet Gynecol 2013; 122:1122-31).

In an embodiment the subject to be tested shall be suspected to suffer from preeclampsia or from a preeclampsia-related condition. In particular, the subject shall be suspected to suffer from preeclampsia. If either hypertension or proteinuria alone is present during pregnancy, the subject is suspected to suffer from preeclampsia. Other symptoms include headache, visual disturbances, right upper quadrant abdominal (epigastric) pain, oedema (swelling of the hands, face or feet) and oliguria (low output of urine)—(NICE 2015; Diagnostic Assessment Programme PlGF-based testing to help diagnose suspected pre-eclampsia). In an embodiment, the subject suspected to suffer from preeclampsia suffers from hypertension as described elsewhere herein.

In a further embodiment, the subject to be tested may be an at risk person for preeclampsia or a preeclampsia-related condition. A risk person for preeclampsia or a preeclampsia-related condition preferably is a female subject being older than 40 years and/or a female subject in the first pregnancy, a female subject having a family history of preeclampsia (e.g., preeclampsia in a mother or sister), a female subject having a prior history of preeclampsia in previous pregnancy, a female subject having a body mass index at or above 35 kg/m$^2$ at first contact, or a female subject having a multiple pregnancy or pre-existing vascular disease such as hypertension or diabetes, e.g. as described in the NICE (National Institute for Health and Care Excellence, Antenatal Care guideline CG62, March 2008).

Further, it is envisaged that the subject to be tested does not suffer from a condition other than preeclampsia or a preeclampsia-related disorder in which IGFBP-7 is or could be increased. For example, it is envisaged that the subject does not suffer from heart failure, acute or chronic kidney injury and/or cancer. Especially, the subject does not suffer from acute kidney injury.

The term "sample" refers to a sample of a body fluid, to a sample of separated cells or to a sample from a tissue or an organ. Samples of body fluids can be obtained by well-known techniques and include, samples of blood, plasma, serum, urine, lymphatic fluid, sputum, ascites, or any other bodily secretion or derivative thereof. Tissue or organ samples may be obtained from any tissue or organ by, e.g., biopsy. Separated cells may be obtained from the body fluids or the tissues or organs by separating techniques such as centrifugation or cell sorting. E.g., cell-, tissue or organ samples may be obtained from those cells, tissues or organs which express or produce the biomarker. The sample may be frozen, fresh, fixed (e.g. formalin fixed), centrifuged, and/or embedded (e.g. paraffin embedded), etc. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample.

In a preferred embodiment, the sample is a blood (i.e. whole blood), serum or plasma sample. Serum is the liquid fraction of whole blood that is obtained after the blood is allowed to clot. For obtaining the serum, the clot is removed by centrifugation and the supernatant is collected. Plasma is the acellular fluid portion of blood. For obtaining a plasma sample, whole blood is collected in anticoagulant-treated tubes (e.g. citrate-treated or EDTA-treated tubes). Cells are removed from the sample by centrifugation and the supernatant (i.e. the plasma sample) is obtained.

The term "measuring" the amount of a biomarker as referred to herein refers to the quantification of the biomarker, e.g. to determining the level of the biomarker in the sample, employing appropriate methods of detection described elsewhere herein. The terms "measuring" and "determining" are used herein interchangeably.

In an embodiment, the amount of a biomarker is measured by contacting the sample with an agent that specifically binds to the biomarker, thereby forming a complex between the agent and said biomarker, detecting the amount of complex formed, and thereby measuring the amount of said biomarker.

The biomarkers as referred to herein can be detected using methods generally known in the art. Methods of detection generally encompass methods to quantify the amount of a biomarker in the sample (quantitative method). It is generally known to the skilled artisan which of the following methods are suitable for qualitative and/or for quantitative detection of a biomarker. Samples can be conveniently assayed for, e.g., proteins using Westerns and immunoassays, like ELISAs, RI-As, fluorescence- and luminescence-based immunoassays, which are commercially available. Further suitable methods to detect biomarker include measuring a physical or chemical property specific for the peptide or polypeptide such as its precise molecular mass or NMR spectrum. Said methods comprise, e.g., biosensors, optical devices coupled to immunoassays, biochips, analytical devices such as mass-spectrometers, NMR-analyzers, or chromatography devices. Further, methods include microplate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

For the detection of biomarker proteins as referred to herein a wide range of immunoassay techniques using such an assay format are available, see, e.g., U.S. Pat. Nos. 4,016,043, 4,424,279, and 4,018,653. These include both single-site and two-site or "sandwich" assays of the non-competitive types, as well as in the traditional competitive binding assays. These assays also include direct binding of a labeled antibody to a target biomarker.

Sandwich assays are among the most useful immunoassays.

Methods employing electrochemiluminescent labels are well-known. Such methods make use of the ability of special metal complexes to achieve, by means of oxidation, an excited state from which they decay to ground state, emitting electrochemiluminescence. For review see Richter, M. M., Chem. Rev. 104 (2004) 3003-3036.

In an embodiment, the detection antibody (or an antigen-binding fragment thereof) to be used for measuring the amount of a biomarker is ruthenylated or iridinylated. Accordingly, the antibody (or an antigen-binding fragment thereof) shall comprise a ruthenium label. In an embodiment, said ruthenium label is a bipyridine-ruthenium(II) complex. Or the antibody (or an antigen-binding fragment thereof) shall comprise an iridium label. In an embodiment, said iridium label is a complex as disclosed in WO 2012/107419.

Measuring the amount of a polypeptide (such as IGFBP-7) may, preferably, comprise the steps of (a) contacting the polypeptide with an agent that specifically binds said polypeptide (b) (optionally) removing non-bound agent, (c) measuring the amount of bound binding agent, i.e. the complex of the agent formed in step (a). According to a preferred embodiment, said steps of contacting, removing and measuring may be performed by an analyzer unit. According to some embodiments, said steps may be performed by a single analyzer unit of said system or by more than one analyzer unit in operable communication with each other. For example, according to a specific embodiment, said system disclosed herein may include a first analyzer unit for performing said steps of contacting and removing and a second analyzer unit, operably connected to said first analyzer unit by a transport unit (for example, a robotic arm), which performs said step of measuring.

The agent which specifically binds the biomarker (herein also referred to as "binding agent") may be coupled covalently or non-covalently to a label allowing detection and measurement of the bound agent. Labeling may be done by direct or indirect methods. Direct labeling involves coupling of the label directly (covalently or non-covalently) to the binding agent. Indirect labeling involves binding (covalently or non-covalently) of a secondary binding agent to the first binding agent. The secondary binding agent should specifically bind to the first binding agent. Said secondary binding agent may be coupled with a suitable label and/or be the target (receptor) of tertiary binding agent binding to the secondary binding agent. Suitable secondary and higher order binding agents may include antibodies, secondary antibodies, and the well-known streptavidin-biotin system (Vector Laboratories, Inc.). The binding agent or substrate may also be "tagged" with one or more tags as known in the art. Such tags may then be targets for higher order binding agents. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium complexes, iridium complexes, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, avail-able as ready-made stock solution from Roche Diagnostics), CDP-Star™ (Amersham Bio-sciences), ECF™ (Amersham Biosciences). A suitable enzyme-substrate combination may result in a colored reaction product, fluorescence or chemoluminescence, which can be measured according to methods known in the art (e.g. using a light-sensitive film or a suit-able camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. A radioactive label can be detected by any method known and appropriate, e.g. a light-sensitive film or a phosphor imager.

The amount of a polypeptide may be, also preferably, measured as follows: (a) contacting a solid support comprising a binding agent for the polypeptide as described elsewhere herein with a sample comprising the peptide or polypeptide and (b) measuring the amount peptide or polypeptide which is bound to the support. Materials for manufacturing supports are well-known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc.

In yet an aspect the sample is removed from the complex formed between the binding agent and the at least one marker prior to the measurement of the amount of formed complex. Accordingly, in an aspect, the binding agent may be immobilized on a solid support. In yet an aspect, the sample can be removed from the formed complex on the solid support by applying a washing solution.

"Sandwich assays" are among the most useful and commonly used assays encompassing a number of variations of the sandwich assay technique. Briefly, in a typical assay, an unlabeled (capture) binding agent is immobilized or can be immobilized on a solid substrate, and the sample to be tested is brought into contact with the capture binding agent. After a suitable period of incubation, for a period of time sufficient to allow formation of a binding agent-biomarker complex, a second (detection) binding agent labeled with a reporter molecule capable of producing a detectable signal is then added and incubated, allowing time sufficient for the formation of another complex of binding agent-biomarkerlabeled binding agent. Any unreacted material may be washed away, and the presence of the biomarker is determined by observation of a signal produced by the reporter molecule bound to the detection binding agent. The results may either be qualitative, by simple observation of a visible signal, or may be quantitated by comparison with a control sample containing known amounts of biomarker.

The incubation steps of a typical sandwich assays can be varied as required and appropriate. Such variations include for example simultaneous incubations, in which two or more of binding agent and biomarker are co-incubated. For example, both, the sample to be analyzed and a labeled binding agent are added simultaneously to an immobilized capture binding agent. It is also possible to first incubate the sample to be analyzed and a labeled binding agent and to thereafter add an antibody bound to a solid phase or capable of binding to a solid phase.

The formed complex between a specific binding agent and the biomarker shall be proportional to the amount of the biomarker present in the sample. It will be understood that the specificity and/or sensitivity of the binding agent to be applied defines the degree of proportion of at least one marker comprised in the sample which is capable of being specifically bound. Further details on how the measurement can be carried out are also found elsewhere herein. The amount of formed complex shall be transformed into an amount of the biomarker reflecting the amount indeed present in the sample.

The terms "binding agent", "specific binding agent", "analyte-specific binding agent", "detection agent" and "agent that specifically binds to a biomarker" are used interchangeably herein. Preferably it relates to an agent that comprises a binding moiety which specifically binds the corresponding biomarker. Examples of "binding agents" or "agents" are a nucleic acid probe, nucleic acid primer, DNA molecule, RNA molecule, aptamer, antibody, antibody fragment, peptide, peptide nucleic acid (PNA) or chemical compound. A preferred agent is an antibody which specifically binds to the biomarker to be measured. The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity (i.e. antigen-binding fragments thereof). Preferably, the antibody is a polyclonal antibody. More preferably, the antibody is a monoclonal antibody.

The term "specific binding" or "specifically bind" refers to a binding reaction wherein binding pair molecules exhibit a binding to each other under conditions where they do not significantly bind to other molecules. The term "specific binding" or "specifically binds", when referring to a protein or peptide as biomarker, refers to a binding reaction wherein a binding agent binds to the corresponding biomarker with an affinity of at least $10^{-7}$ M. The term "specific binding" or "specifically binds" preferably refers to an affinity of at least $10^{-8}$ M or even more preferred of at least $10^{-9}$ M for its target molecule. The term "specific" or "specifically" is used to indicate that other molecules present in the sample do not significantly bind to the binding agent specific for the target molecule.

In accordance with the present invention, the amount of Insulin-like Growth Factor Binding Protein 7 (=IGFBP-7) shall be measured. Preferably, the amount of the IGFBP-7 polypeptide is measured. IGFBP-7 is a 30-kDa modular glycoprotein known to be secreted by endothelial cells, vascular smooth muscle cells, fibroblasts, and epithelial cells (Ono, Y., et al., Biochem Biophys Res Comm 202 (1994) 1490-1496). Preferably, the term "IGFBP-7" refers to human IGFBP-7. The sequence of the protein is well-known in the art and is e.g. accessible via Uni-Prot (Q16270, IBP7_HUMAN), or via GenBank (NP_001240764.1). A detailed definition of the biomarker IGFBP-7 is e.g. provided in WO 2008/089994 which herewith is incorporated by reference in its entirety. There are two isoforms of IGFBP-7, Isoform 1 and 2 which are produced by alternative splicing. In an embodiment of the present invention, the total amount of both isoforms is measured (for the sequence, see the UniProt database entry (Q16270-1 and Q16270-2).

In one embodiment, the method of the present invention is based on detecting a protein complex comprising human IGFBP-7 and a non-human or chimeric IGFBP-7-specific binding agent. In such embodiment the present invention reads on a method for diagnosing preeclampsia or a preeclampsia-related condition in a pregnant human subject, said method comprising the steps of (a) incubating a sample from said subject with a non-human IGFBP-7-specific binding agent (b) measuring the complex between the IGFBP-7-specific binding agent and IGFBP-7 formed in (a), and (c) comparing the measured amount complex to a reference amount. An amount of the complex at or above the reference amount is indicative for preeclampsia or a preeclampsia-related disorder.

The term "amount" as used herein encompasses the absolute amount of a biomarker as referred to herein, the relative amount or concentration of the said biomarker as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response amounts measured from biological read out systems in response to the peptides or intensity signals obtained from specifically bound ligands. It is to be understood that values correlating to the aforementioned amounts or parameters can also be obtained by all standard mathematical operations.

The term "comparing" as used herein refers to comparing the amount of the biomarker in the sample from the subject with the reference amount of the biomarker specified elsewhere in this description. It is to be understood that comparing as used herein usually refers to a comparison of corresponding parameters or values, e.g., an absolute amount is compared to an absolute reference amount while a concentration is compared to a reference concentration or an intensity signal obtained from the biomarker in a sample is compared to the same type of intensity signal obtained from a reference sample. The comparison may be carried out manually or computer-assisted. Thus, the comparison may be carried out by a computing device. The value of the measured or detected amount of the biomarker in the sample from the subject and the reference amount can be, e.g., compared to each other and the said comparison can be automatically carried out by a computer program executing an algorithm for the comparison. The computer program carrying out the said evaluation will provide the desired assessment in a suitable output format. For a computer-assisted comparison, the value of the measured amount may be compared to values corresponding to suitable references which are stored in a database by a computer program. The computer program may further evaluate the result of the comparison, i.e. automatically provide the desired assessment in a suitable output format. For a computer-assisted comparison, the value of the measured amount may be compared to values corresponding to suitable references which are stored in a database by a computer program. The computer program may further evaluate the result of the comparison, i.e. automatically provides the desired assessment in a suitable output format.

In accordance with the present invention the amount of the biomarker IGFBP-7 shall be compared to a reference. The reference is preferably a reference amount. The term "reference amount" as used herein refers to an amount which allows for allocation of a subject into either (i) the group of subjects suffering from preeclampsia or a preeclampsia-related condition or (ii) the group of subjects not suffering from preeclampsia or a preeclampsia-related condition. A suitable reference amount may be determined from a reference sample to be analyzed together, i.e. simultaneously or subsequently, with the test sample.

Reference amounts can, in principle, be calculated for a cohort of subjects as specified above based on the average or mean values for a given biomarker by applying standard methods of statistics. In particular, accuracy of a test such as a method aiming to diagnose an event, or not, is best described by its receiver-operating characteristics (ROC) (see especially Zweig 1993, Clin. Chem. 39:561-577). The ROC graph is a plot of all of the sensitivity versus specificity pairs resulting from continuously varying the decision threshold over the entire range of data observed. The clinical performance of a diagnostic method depends on its accuracy, i.e. its ability to correctly allocate subjects to a certain prognosis or diagnosis. The ROC plot indicates the overlap between the two distributions by plotting the sensitivity versus 1—specificity for the complete range of thresholds suitable for making a distinction. On the y-axis is sensitivity, or the true-positive fraction, which is defined as the ratio of number of true-positive test results to the product of number of true-positive and number of false-negative test results. This has also been referred to as positivity in the presence of a disease or condition. It is calculated solely from the affected subgroup. On the x-axis is the false-positive fraction, or 1—specificity, which is defined as the ratio of number of false-positive results to the product of number of true-negative and number of false-positive results. It is an index of specificity and is calculated entirely from the unaffected subgroup. Because the true- and false-positive fractions are calculated entirely separately, by using the test results from two different subgroups, the ROC plot is independent of the prevalence of the event in the cohort. Each point on the ROC plot represents a sensitivity/1—specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. If the ROC plot falls completely below the 45° diagonal, this is easily remedied by reversing the criterion for "positivity" from "greater than" to "less than" or vice versa. Qualitatively, the closer the plot is to the upper left corner, the higher the overall accuracy of the test. Dependent on a desired confidence interval, a threshold can be derived from the ROC curve allowing for the diagnosis for a given event with a proper balance of sensitivity and specificity, respectively. Accordingly, the reference to be used for the aforementioned method of the present invention, i.e. a threshold which allows to differentiating between subjects suffering from preeclampsia or a preeclampsia-related condition or those not suffering preeclampsia or a preeclampsia-related condition among a cohort of pregnant subject can be generated, preferably, by establishing a ROC for said cohort as described above and deriving a threshold amount therefrom. Dependent on a desired sensitivity and specificity for a diagnostic method, the ROC plot allows deriving a suitable threshold. It will be understood that an optimal sensitivity is desired for excluding a subject suffering from preeclampsia or a preeclampsia-related condition (i.e. a rule out) whereas an optimal specificity is envisaged for a subject to be assessed as suffering from preeclampsia or a preeclampsia-related condition (i.e. a rule in).

In certain embodiments, the term "reference amount" herein refers to a predetermined value. Said predetermined value shall allow for differentiating between a subject suffering from preeclampsia or a preeclampsia-related condition and a subject not suffering from preeclampsia or a preeclampsia-related condition.

Preferably, an amount of IGFBP-7 in the sample of the test subject at or above the reference amount indicates that the subject suffers from preeclampsia or a preeclampsia-related condition. Also preferably, an amount of IGFBP-7 in the sample below the reference amount indicates that the subject does not suffer from preeclampsia or a preeclampsia-related condition.

In an embodiment, the reference amount is derived from a pregnant subject or a group of pregnant subjects known not to suffer from the disease or condition to be diagnosed (i.e. from preeclampsia or a preeclampsia-related condition. Preferably, the reference amount is derived from a pregnant subject or group of pregnant subjects being at the same stage (e.g. trimester, month or week) of gestation as the subject to be tested.

If i) the reference amount is derived from a pregnant subject or a group of pregnant subjects known not to suffer from the disease or condition to be diagnosed, an amount of the biomarker IGFBP-7 in the sample of the subject which is decreased as compared to the reference amount, is indicative for a subject who does not suffer from preeclampsia or a preeclampsia-related condition.

If ii) the reference amount is derived from a pregnant subject or a group thereof known to not to suffer from the disease or condition to be diagnosed, an amount of the biomarker IGFBP-7 in the sample of the subject which is the same as the reference amount or which is increased as compared to the reference amount, is indicative for a subject who suffers from preeclampsia or a preeclampsia-related condition.

In an embodiment, the reference amount is within a range of about 70 to 110 ng/ml, especially within 80 to 90 ng/ml. For example, the reference amount is an amount of about 85 ng/ml.

In an embodiment of the method of the invention, said method further comprises a step of recommending and/or initiating at least one suitable supportive measure according to the comparison results. Preferably, said at least one suitable supportive measure is recommended or initiated if the subject suffers from preeclampsia or a preeclampsia-related condition.

The term "recommending" as used herein means establishing a proposal for a suitable supportive measure which could be applied to the subject. The suitable supportive measure refers to all measures which can be applied to subjects suffering from preeclampsia or preeclampsia-related condition in order to cure, avoid or handle the said health condition. For example, patient management measures include degree of monitoring (e.g., close, regular or weak monitoring), hospitalization or ambulant maintenance, applying or refraining from drug treatment, or life style recommendations. In particular, said at least one suitable supportive measure is selected from the group consisting of: close monitoring, admittance to an intensive care unit, administration of corticosteroids, admission of magnesium sulfate, and administration of blood pressure reducing agents.

As disclosed above a diagnosis can be based on the comparison step carried out in step b). However, it is also contemplated to additionally determine the amounts of further biomarkers for the diagnosis.

In an embodiment of the present invention, the method comprises the measurement of the amount(s) of at least one further biomarker selected from the group of sFlt-1 (Soluble fms-like tyrosine kinase-1), Endoglin and PlGF (Placental Growth Factor) in a sample from the subject.

In an embodiment, the measurement of the amount(s) of said at least one further biomarker is done for diagnosing preeclampsia.

The term "sFlt-1" as used herein refers to a polypeptide which is a soluble form of the fms-like tyrosine kinase 1. The polypeptide is also referred to as soluble VEGF receptor 1 (sVEGF R1) in the art (see, e.g., Sunderji 2010, Am J Obstet Gynecol 202: 40e1-7). sFlt-1 was identified in conditioned culture medium of human umbilical vein endothelial cells. The endogenous sFlt-1 receptor is chromatographically and immunologically similar to recombinant human sFlt-1 and binds [125I] VEGF with a comparable high affinity. Human sFlt-1 is shown to form a VEGF-stabilized complex with the extracellular domain of KDR/Flk-1 in vitro. Preferably, sFlt-1 refers to human sFlt-1 as described in Kendall 1996, Biochem Biophys Res Commun 226(2): 324-328; for amino acid sequences see, e.g., also GenBank accession numbers P17948, GI: 125361 for human and BAA24499.1, GI: 2809071 for mouse sFlt-1.

Endoglin is a type I membrane glycoprotein located on cell surfaces and is part of the TGF (Transforming growth factor) beta receptor complex. It is polypeptide having a molecular weight of about 180 kDa non-reduced, about 95 kDa after reduction and about 66 kDa in its reduced and N-deglycosylated form. Preferably, the term "Endoglin" refers to soluble Endoglin. The polypeptide is capable of forming dimers and binds to TGF-β and TGF-β receptors. Preferably, Endoglin refers to human Endoglin. More preferably, human Endoglin has an amino acid sequence as shown in GenBank accession number AAC63386.1, GI: 3201489. Two Endoglin isoforms, S-Endoglin and L-Endoglin have been described. L-Endoglin consists of total of 633 amino acids with a cytoplasmic tail of 47 amino acids while S-Endoglin consists of 600 amino acids with a cytoplasmic tail of 14 amino acids.

The term "PlGF (Placental Growth Factor)" as used herein, preferably, refers to a placenta-derived growth factor which is a polypeptide having 149 amino acids in length and being highly homologous to the platelet-derived growth factor-like region of human vascular endothelial growth factor (VEGF). Like VEGF, PlGF has angiogenic activity in vitro and in vivo. For example, biochemical and functional characterization of PlGF derived from transfected COS-1 cells revealed that it is a glycosylated dimeric secreted protein which is able to stimulate endothelial cell growth in vitro (Maqlione 1993, Oncogene 8(4):925-31). Preferably, PlGF refers to human PlGF, more preferably, to human PlGF having an amino acid sequence as shown in GenBank accession number P49763, GI: 17380553.

The amount(s) of the further biomarker(s) can be measured in the same sample as the amount of IGFBP-7 or in a different sample. In particular, the amounts are measured in the same sample or an aliquot thereof.

Preferably, the amounts of two further biomarkers selected from of sFlt-1 (Soluble fms-like tyrosine kinase-1), Endoglin and PlGF (Placental Growth Factor) are measured. More preferably, the amounts of the biomarkers Endoglin and PlGF are measured. More preferably, the amounts of the biomarkers sFlt-1 and PlGF are measured.

If the amounts of two further biomarkers as described above are measured, the method of the present invention may comprise the further step of calculating a ratio of the amounts of the two biomarkers. For example, a ratio of the amounts of (i) the biomarkers sFlt-1 and PlGF or (ii) the biomarkers Endoglin and PlGF can be calculated. In a further step, the calculated ratio is compared to a reference ratio. The diagnosis of preeclampsia or a preeclampsia-related condition is preferably based on the results of the comparison of the calculated ratio to the reference ratio and on the comparison of the amount of IGFBP-7 to the reference amount.

The term "calculating a ratio" as referred to herein relates to calculating a ratio of the amount of sFlt-1 or Endoglin and the amount of PlGF by dividing the said amount or by carrying out any other comparable mathematical calculation which puts into a relation the amount of sFlt-1 or Endoglin towards the amount of PlGF. Preferably, the amount of sFlt-1 or Endoglin is divided by the amount of PlGF in order to calculate the ratio (thus, the ratio of the amount of sFlt-1 or Endoglin to the amount of PlGF is calculated). Also preferably, the amount of PlGF is divided by the amount of sFlt-1 or Endoglin in order to calculate the ratio (thus, the ratio of the amount of PlGF to the amount of sFlt-1 or Endoglin is calculated).

The reference ratio shall allow for differentiating between subjects suffering from preeclampsia or a preeclampsia-related condition and between subjects not suffering from preeclampsia or a preeclampsia-related condition. In an embodiment, the reference ratio is determined as described herein above for the reference amount.

In an embodiment, the ratio of sFlt-1 to PlGF, or of Endoglin to PlGF is calculated. Thus, the reference ratio shall be a reference ratio of sFlt-1 to PlGF, or of Endoglin to PlGF. Preferably, an amount of IGFBP-7 at or above the reference amount in combination with a ratio of sFlt-1 to PlGF, or of Endoglin to PlGF at or above the reference ratio indicates that the subject suffers from preeclampsia or a preeclampsia-related condition. Also preferably, an amount of IGFBP-7 below the reference amount in combination with a ratio of sFlt-1 to PlGF, or of Endoglin to PlGF below the reference ratio indicates that the subject does not suffer from preeclampsia or a preeclampsia-related condition.

One embodiment relates to a method for diagnosing preeclampsia in a pregnant subject, said method comprising the steps of (a) measuring the amount of IGFBP-7 (Insulin-like Growth Factor Binding Protein 7) in a sample from the subject, (b) measuring the ratio of at least one of (i) the biomarkers sFlt-1 and PlGF, or (ii) the biomarkers Endoglin and PlGF, (c) blood pressure, and (d) comparing the measured amount of the biomarker in (a), the ratio measured in (b) and the blood pressure measured in (c) to a reference.

The definitions and explanations given herein above apply mutatis mutandis to the following method for assessing the severity of preeclampsia or a preeclampsia-related condition and to the following method for monitoring preeclampsia or a preeclampsia-related condition.

The method according to the present invention in one embodiment relates to assessing the severity of preeclampsia or a preeclampsia-related condition in a subject suffering from preeclampsia or a preeclampsia-related condition, said method comprising the steps of
(a) measuring the amount of the biomarker IGFBP-7 (Insulin-like Growth Factor Binding Protein 7) in a sample from the subject, and
(b) comparing the measured amount of the biomarker to a reference.

In an embodiment of the aforementioned method of the present invention, the severity of preeclampsia or a preeclampsia-related condition is assessed by carrying out the further step of c) assessing the severity of preeclampsia or a preeclampsia-related condition. Said assessment shall be based on the result of the comparison carried out in step b).

Preferably, the method is an in vitro method.

The expression "assessing the severity of preeclampsia or a preeclampsia-related condition" as used herein preferably refers to differentiating between a mild form and a severe form of preeclampsia or a preeclampsia-related condition. Also preferably, the term relates to the staging of preeclampsia or a preeclampsia-related condition. In general, the more increased the amount of IGFBP-7 in the sample from the subject is, the more severe the disease or condition to be assessed.

Mild forms and severe forms of preeclampsia or a preeclampsia-related condition are known by the skilled person. In addition, the expressions "mild form of preeclampsia" and "severe form of preeclampsia" are defined herein above in connection with the method of diagnosing preeclampsia or a preeclampsia-related condition. The definition applies accordingly.

The term "subject" has been defined above. The definition applies accordingly. However, in the context to the aforementioned method it is envisaged that the subject suffers from preeclampsia or a preeclampsia-related condition. E.g., the severity of preeclampsia shall be assessed in a subject (such as a pregnant subject) suffering from preeclampsia or the severity of proteinuria in a subject suffering from proteinuria.

In a preferred embodiment of the aforementioned method, the severity of proteinuria in a pregnant subject suffering from preeclampsia is assessed. In another preferred embodiment, the severity of proteinuria in a pregnant subject suspected to suffer from preeclampsia is assessed.

The reference to be applied is preferably a reference amount. In a preferred embodiment of the aforementioned method, the reference amount is a predetermined value. Said predetermined value shall allow for differentiating between a mild and a severe form of preeclampsia or a preeclampsia-related condition. Preferably, an amount of IGFBP-7 in the sample from the subject above the reference amount indicates that the subject suffers from a severe form of preeclampsia or a preeclampsia-related condition. Also preferably, an amount of IGFBP-7 in the sample from the subject below the reference amount indicates that the subject does not suffer from a severe form of preeclampsia or a preeclampsia-related condition. Thus, the subject suffers from a mild form of preeclampsia or a preeclampsia-related condition.

The method of assessing the severity of preeclampsia or a preeclampsia-related condition may further comprise the measurement of the amount of at least one biomarker selected from the group of sFlt-1 (Soluble fms-like tyrosine kinase-1), Endoglin and PlGF (Placental Growth Factor) in a sample from the subject (as described above for the method of diagnosing preeclampsia or a preeclampsia-related condition). In an embodiment, the amounts of the biomarkers sFlt-1 and PlGF are measured. In an alternative embodiment, the amounts of the biomarkers Endoglin and PlGF are measured.

Further, it is envisaged to calculate a ratio of the amounts of (i) the biomarkers sFlt-1 and PlGF or (ii) the biomarkers Endoglin and PlGF (as described above). In a further step, the thus calculated ratio is compared to a reference ratio. The assessment of the severity of preeclampsia or a preeclampsia-related condition is preferably based on the results of the comparison of the calculated ratio to the reference ratio and on the comparison of the amount of IGFBP-7 to the reference amount.

The reference ratio shall allow for differentiating between a severe form of preeclampsia or a preeclampsia-related condition and a mild form of preeclampsia or a preeclampsia-related condition. In an embodiment, the reference ratio is determined as described herein above.

In an embodiment, the ratio of sFlt-1 to PlGF, or of Endoglin to PlGF is calculated. Thus, the reference ratio shall be a reference ratio of sFlt-1 to PlGF, or of Endoglin to PlGF. Preferably, an amount of IGFBP-7 above the reference amount in combination with a ratio of sFlt-1 to PlGF, or of Endoglin to PlGF above the reference ratio indicates that the subject suffers from a severe preeclampsia or a preeclampsia-related condition. Also preferably, an amount of IGFBP-7 below the reference amount in combination with a ratio of sFlt-1 to PlGF, or of Endoglin to PlGF below the reference ratio indicates that the subject suffers from a mild form of preeclampsia or a preeclampsia-related condition.

The present invention further relates to a method for monitoring preeclampsia or a preeclampsia-related condition in a subject suffering therefrom, comprising the steps of
(a) measuring the amount of the biomarker IGFBP-7 in a first sample from the subject,
(b) measuring the amount of the biomarker IGFBP-7 in a second sample from the subject, and
(c) comparing the amount of the biomarker in the second sample to the amount of the biomarker in the first sample.

Preferably, the monitoring of preeclampsia or a preeclampsia-related condition is based on the results of the comparison step c).

Preferably, the aforementioned method is an in vitro method.

As used herein, the term "monitoring" refers to assessing the course of preeclampsia or a preeclampsia or a preeclampsia-related condition in a subject (e.g. in a pregnant subject).

In an embodiment of the aforementioned method, the proteinuria in a pregnant subject suffering from preeclampsia is monitored. In another embodiment, the proteinuria in a pregnant subject suspected to suffer from preeclampsia is monitored.

The term "sample" has been defined above. The definition applies accordingly. The first sample as referred to in the context of the aforementioned method can be obtained at any time after the onset of preeclampsia or a preeclampsia-related condition. The second sample shall be obtained after the first sample. Preferably, the second sample is not obtained too early after the first sample (in order to observe a sufficiently significant change to allow for monitoring). Thus, the second sample is preferably obtained within 1 to 30 days, more preferably within 2 to 14 days, and most preferably within 2 to 7 days after the first sample. Further, it is contemplated that the second sample is obtained as least one day after the first sample.

The term "comparing" as used in connection with the aforementioned method encompasses comparing the amount of the biomarker IGFBP-7 in a second sample with an amount of said biomarker in the first sample. Preferably, an increase, and more preferably a statistically significant increase of the amount of IGFBP-7 in said second sample compared to the amount in said first sample indicates deterioration of preeclampsia or the preeclampsia-related condition. Thus, the preeclampsia or the preeclampsia-related condition has deteriorated during the period between obtaining the first and the second sample. Preferably, a decrease of the amount of IGFBP-7 in said second sample as compared to said first sample indicates amelioration of preeclampsia or the preeclampsia-related condition. Thus, the preeclampsia or the preeclampsia-related condition has improved during the period between obtaining the first and the second sample. Particularly, a significant increase (or decrease) is an increase (or decrease) of a size which is considered to be significant for, particularly statistically significant. The terms "significant" and "statistically significant" are known to the person skilled in the art. Whether an increase (or decrease) is statistically significant can be determined without further ado by the person skilled in the art using various well-known statistic evaluation tools. Preferably, a statistically significant increase (or decrease) is an increase (or decrease) of at least 5%.

An unchanged amount, in particular an essentially unchanged amount, in said second sample as compared to said first sample, preferably, indicates no change in status of said preeclampsia or preeclampsia-related condition.

The method of monitoring preeclampsia or a preeclampsia-related condition may further comprise the measurement of the amount of at least one biomarker selected from the group of sFlt-1 (Soluble fms-like tyrosine kinase-1), Endoglin and PlGF (Placental Growth Factor) in a sample from the subject in the first and second sample from the subject.

Further, it is envisaged to calculate a ratio of the amounts of (i) the biomarkers sFlt-1 and PlGF or (ii) the biomarkers Endoglin and PlGF for the first and second sample. In a further step, the thus calculated ratio for the second sample is compared to the calculated ratio for the first sample. Monitoring preeclampsia or a preeclampsia-related condition is preferably based on the results of the comparison of the calculated ratios and on the amounts of IGFBP-7 in the second and first sample.

In an embodiment, the ratio of sFlt-1 to PlGF, or of Endoglin to PlGF is calculated for the first and second sample. Preferably, an amount of IGFBP-7 in the second sample which is increased as compared to amount in the first sample in combination with a ratio of sFlt-1 to PlGF in the second sample which is increased as compared to ratio in the first sample indicates deterioration of preeclampsia or the preeclampsia-related condition. Also preferably, an amount of IGFBP-7 in the second sample which is decreased as compared to amount in the first sample in combination with a ratio of sFlt-1 to PlGF in the second sample which is decreased as compared to ratio in the first sample indicates amelioration of preeclampsia or the preeclampsia-related condition.

The definitions and explanations given herein above apply mutatis mutandis to the following:

Moreover, the present invention relates to the use of
i) the biomarker IGFBP-7, and optionally of at least one further biomarker selected from the group of sFlt-1 (Soluble fms-like tyrosine kinase-1), Endoglin and PlGF (Placental Growth Factor), or
ii) an agent that specifically binds to IGFBP-7, and optionally of at least one further agent selected from the group of an agent that specifically binds to sFlt-1, an agent that specifically binds to Endoglin, and an agent that specifically binds to PlGF, in a sample from a subject for diagnosing preeclampsia or a preeclampsia-related condition.

Further, the present invention relates to the use of
i) the biomarker IGFBP-7, and optionally of at least one further biomarker selected from the group of sFlt-1 (Soluble fms-like tyrosine kinase-1), Endoglin and PlGF (Placental Growth Factor), or
ii) an agent that specifically binds to IGFBP-7, and optionally of at least one further agent selected from the group of an agent that specifically binds to sFlt-1, an agent that specifically binds to Endoglin, and an agent that specifically binds to PlGF,
in a sample from a subject for assessing the severity of preeclampsia or a preeclampsia-related condition.

Also, the present invention relates to the use of
i) the biomarker IGFBP-7, and optionally of at least one further biomarker selected from the group of sFlt-1 (Soluble fms-like tyrosine kinase-1), Endoglin and PlGF (Placental Growth Factor), or
ii) an agent that specifically binds to IGFBP-7, and optionally of at least one further agent selected from the group of an agent that specifically binds to sFlt-1, an agent that specifically binds to Endoglin, and an agent that specifically binds to PlGF,
in a first and second sample from a subject for monitoring preeclampsia or a preeclampsia-related condition.

In an embodiment of the three aforementioned uses
i) the biomarkers IGFBP-7, sFlt-1, and PlGF, or
ii) an agent that specifically binds to IGFBP-7, an agent that specifically binds to sFlt-1, and an agent that specifically binds to PlGF,
are used.

The aforementioned uses are preferably in vitro uses.

The "agent that specifically binds to a biomarker" has been defined above. The definition applies accordingly. In an embodiment, said agent is an antibody or antigen-binding fragment thereof which specifically binds to the respective biomarker.

The present invention also relates to a kit adapted for carrying out the method of the present invention comprising an agent which specifically binds IGFBP-7 and optionally instructions for carrying out the said method. The kit may further comprise at least one further agent selected from the group of an agent that specifically binds to sFlt-1, an agent that specifically binds to Endoglin, and an agent that specifically binds to PlGF. In an embodiment, the kit further comprises an agent that specifically binds to sFlt-1 and an agent that specifically binds to PlGF. In an alternative embodiment, the kit further comprises an agent that specifically binds to Endoglin and an agent that specifically binds to PlGF.

The term "kit" as used herein refers to a collection of the aforementioned components, preferably, provided separately or within a single container. The container also comprises instructions for carrying out the method of the present invention. These instructions may be in the form of a manual or may be provided by a computer program code which is capable of carrying out the calculations and comparisons referred to in the methods of the present invention and to establish a diagnosis accordingly when implemented on a computer or a data processing device. The computer program code may be provided on a data storage medium or device such as an optical storage medium (e.g., a Compact Disc) or directly on a computer or data processing device. Moreover, the kit may, preferably, comprise standard amounts for the biomarker IGFBP-7 for calibration purposes.

Moreover, the present invention relates to a device adapted for diagnosing whether a subject suffers from preeclampsia or a preeclampsia-related condition, preferably, by carrying out the method of the present invention comprising:
- a) an analyzing unit comprising at least one agent which specifically binds IGFBP-7, said unit being adapted for measuring the amount of IGFBP-7 in a sample of a subject; and
- b) an evaluation unit comprising a stored reference and a data processor having implemented an algorithm for comparing the amount of IGFBP-7 measured by the analyzing unit of (a) with the stored reference, whereby preeclampsia or a preeclampsia-related condition is diagnosed.

The methods of the present invention can be implemented by the aforementioned device. A device as used herein shall comprise at least the aforementioned units. The units of the device are operatively linked to each other. How to link the units in an operating manner will depend on the type of units included into the device. For example, where means for automatically quantitatively measuring IGFBP-7 are applied in an analyzing unit, the data obtained by said automatically operating unit can be processed by the evaluation unit, e.g., by a computer program which runs on a computer being the data processor in order to facilitate the diagnosis. In an embodiment, the data processor executes the comparison of the amount of the biomarker with the reference.

Preferably, the units are comprised by a single device in such a case. However, the analyzing unit and the evaluation unit may also be physically separate. In such a case operative linkage can be achieved via wire and wireless connections between the units which allow for data transfer. A wireless connection may use Wireless LAN (WLAN) or the internet. Wire connections may be achieved by optical and non-optical cable connections between the units. The cables used for wire connections are, preferably, suitable for high throughput data transport.

A preferred analyzing unit for determining IGFBP-7 comprises an agent, such as an antibody (or antigen-binding fragment thereof) which specifically recognizes IGFBP-7 as specified elsewhere herein, and a zone for contacting said detection agent with the sample to be tested. The agent may be immobilized on the zone for contacting or may be applied to said zone after the sample has been loaded. The analyzing unit shall be, preferably, adapted for quantitatively measuring the amount of complexes of the agent and IGFBP-7.

In a preferred embodiment of the device of the present invention, said stored reference is a pre-determined value (as described elsewhere herein). Preferably, an amount of the biomarker IGFBP-7 which is above the reference amount is indicative for a subject suffering from preeclampsia or a preeclampsia-related condition.

In another preferred embodiment of the device of the present invention, said stored reference is a reference amount derived from a subject or a group of subjects known to not suffer from from preeclampsia or a preeclampsia-related condition, or a reference amount derived from a subject or a group of subjects known to suffer from from preeclampsia or a preeclampsia-related condition.

In an embodiment, the analyzing unit comprised by the device of the present invention further comprises an agent that specifically binds to sFlt-1 (or Endoglin) and an agent that specifically binds to PlGF. In this embodiment, the evaluation unit preferably further comprises a stored reference ratio and the implement algorithm shall further allow for comparing a calculated ratio of the amounts of sFlt-1 (or Endoglin) and PlGF (as described elsewhere) to a reference ratio. Preferably, the evaluation unit also comprises means for calculating the ratio of the amounts.

All references cited in this specification are herewith incorporated by reference with respect to their entire disclosure content and the disclosure content specifically mentioned in this specification.

EXAMPLES

The invention will be merely illustrated by the following Examples. The said Examples shall, whatsoever, not be construed in a manner limiting the scope of the invention.

Example 1

Development of an Immunoassay for Fully Automated Quantification of IGFBP-7 in Serum or Plasma An Elecsys IGFBP-7 immunoassay for the fully automated quantification of the analyte IGFBP-7 in serum or plasma on the COBAS platform (Roche Diagnostics) has been developed.

FIG. 1 shows that the IGFBP-7 serum levels are increased with increasing amounts of protein in urine detected by protein dipstick results in pregnant women.

Figure 2:
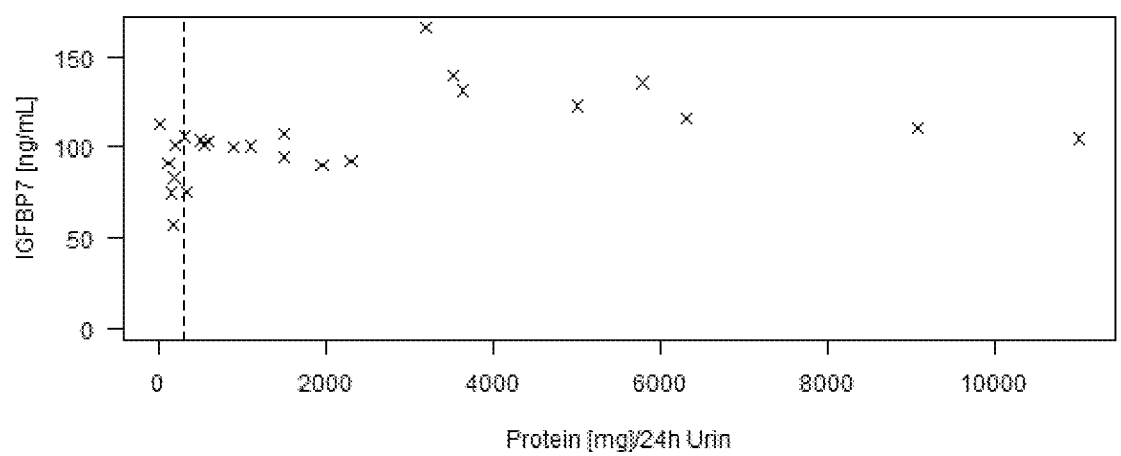
FIG. 2: Scatter diagram of all patients with protein[mg]/24 h urin against IGFBP-7 [ng/ml]. The IGFBP-7 serum levels are increased above a threshold in pregnant women with proteinuria defined as the urinary excretion of more than 300 mg protein in a 24-hour period (Protein [mg]/24 Urine) illustrated by the vertical dashed line in FIG. 2. A threshold of 85 ng/mL was used.

The IGFBP-7 serum levels are increased (see FIG. 2) above a threshold in pregnant women with proteinuria defined as the urinary excretion of more than 300 mg protein in a 24-hour period (Protein [mg]/24 Urine) illustrated by the vertical dashed line in FIG. 2. Thus, a threshold of about 85 ng/mL for high sensitivity is suggested.

Figure 3:
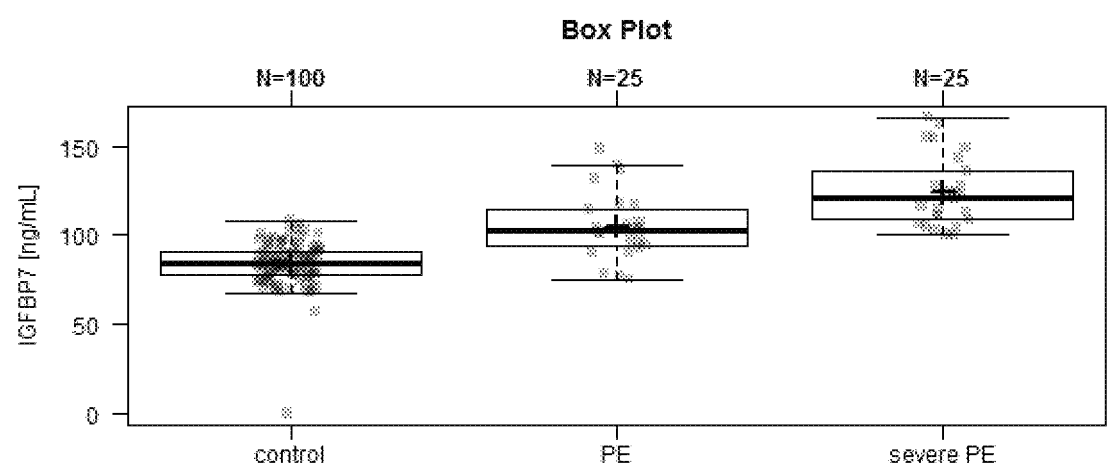
FIG. 3: Boxplots for IGFBP-7 [ng/ml] divided by control group, PE (Preeclampsia) group and severe PE group. The IGFBP-7 serum levels are increased in pregnant women with diagnosed preeclampsia and severe preeclampsia compared to control women having no preeclampsia/severe preeclampsia/ intrauterine growth restriction (IUGR). The mean value of serum IGFBP-7 is more increased in cases of severe preeclampsia (severe PE) than in women with preeclampsia (PE). Therefore the IGFBP-7 serum levels reflect the severity of preeclampsia being defined according to American College of Obstetricians and Gynecologists: Diagnosis and Management of Preeclampsia and Eclampsia. ACOG Practice Bulletin No. 33. Obstet Gynecol 2002; 99: 159-67.
Figure 4:
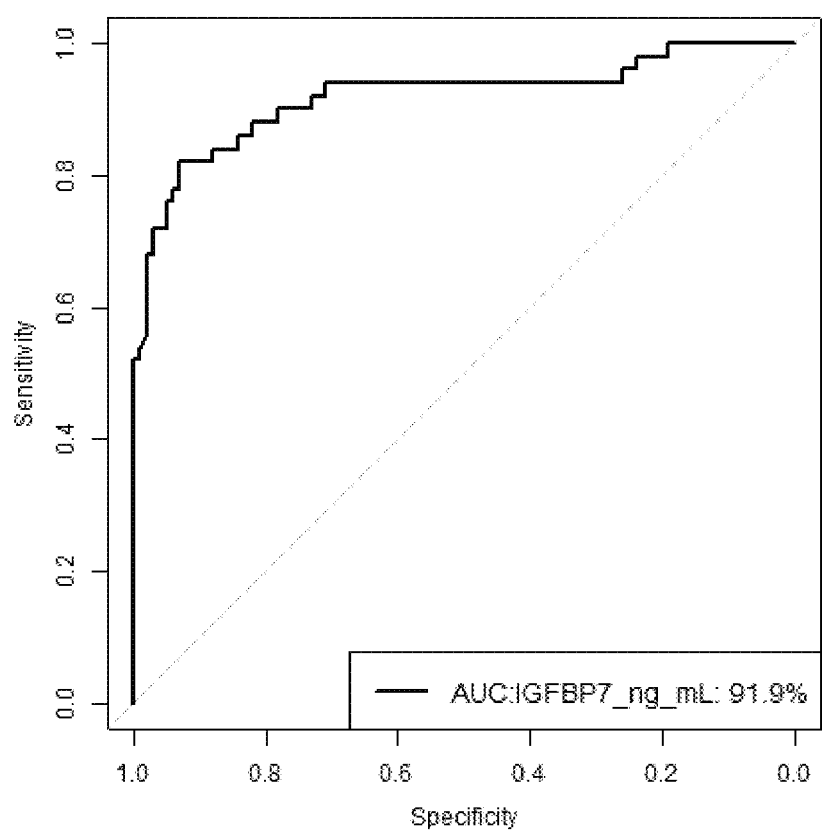
FIG. 4: ROC curve for sFlt-1/PlGF ratio and IGFBP-7 for control group and PE and severe PE cases. In the ROC curve for serum IGFBP-7 for distinguishing pregnant women without preeclampsia/HELLP syndrome (controls, n=100) and pregnant women with diagnosed preeclampsia the AUC is 91.9%. The preeclampsia group (n=50) comprises PE and severe PE cases. Preeclampsia is defined here according to the new onset of hypertension and proteinuria after gestational week 20.

The IGFBP-7 serum levels are increased in pregnant women with diagnosed preeclampsia and severe preeclampsia compared to control women having no preeclampsia/ severe preeclampsia/ intrauterine growth restriction (IUGR). The mean value of serum IGFBP-7 is more increased in cases of severe preeclampsia (severe PE) than in women with preeclampsia (PE). Therefore the IGFBP-7 serum levels seem to reflect the severity of preeclampsia being defined according to American College of Obstetricians and Gynecologists: Diagnosis and Management of Preeclampsia and Eclampsia. ACOG Practice Bulletin No. 33. Obstet Gynecol 2002; 99: 159-67. FIG. 3 shows Boxplots for IGFBP-7 [ng/ml] divided by control group, PE group and severe PE group. A ROC analysis of IGFBP-7 with diagnosed preeclampsia/eclampsia versus controls is shown in FIG. 4. In the ROC curve for serum IGFBP-7 for distinguishing pregnant women without preeclampsia/HELLP syndrome (controls, n=100) and pregnant women with diagnosed preeclampsia the AUC is 91.9%. The preeclampsia group (n=50) comprises PE and severe PE cases (see FIG. 4 and Table 1). Preeclampsia is defined here according to the new onset of hypertension and proteinuria after gestational week 20.

TABLE 1

| | | | Summary table for ROC curve. Group PE and severe PE. | | | | |
|---|---|---|---|---|---|---|---|
| Cases | N_Cases | Controls | N_Controls | AUC | AUC_CI | Sens@90 | Spec@90 |
| Ca. | 50 | Contr. | 100 | 91.9% | [86.4%, 97.4%] | 0.0% | 100.0% |

Example 2

Calculation of ROC Curves for IGFBP-7 and sFlt-1/PlGF Ratio in Patients Diagnosed with Preeclampsia A ROC Analysis of IGFBP-7 and sFlt-1/PlGF of preeclampsia versus controls is shown in FIGS. 5 to 10 and Tables 2 to 7. The combination of IGFBP-7 and sFlt-1/PlGF allows for more specific diagnosis of preeclampsia/eclampsia/HELLP syndrome.

1. ROC Results for PE and Severe PE Cases

Figure 5:
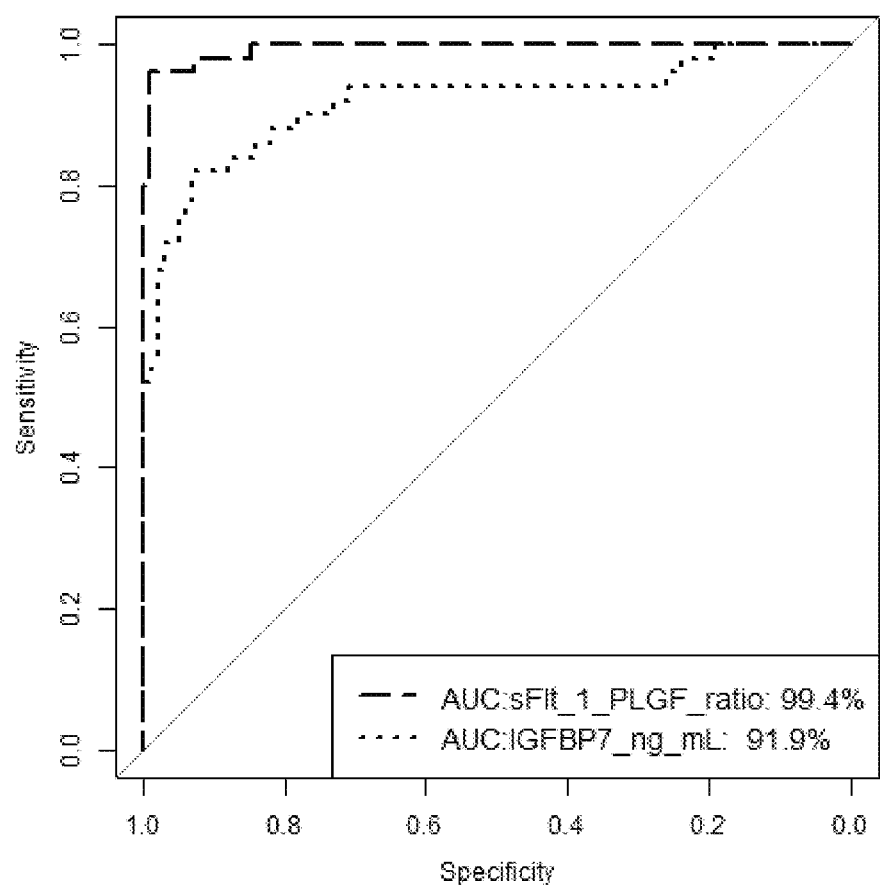
FIG. 5: ROC curve for sFlt-1/PlGF ratio and IGFBP-7 for control group and PE and severe PE cases.

An analysis of IGFBP-7 and sFlt-1/PlGF separately is shown in FIG. 5 and Table 2.

TABLE 2

| | summary table for ROC curve. Severe PE and PE cases | | | | |
|---|---|---|---|---|---|
| variable | threshold | Sens | Sens_CI | Spec | Spec_CI |
| IGFBP-7_ng_mL | 101.8 | 72.0% | [57.5%, 83.8%] | 95.0% | [88.7%, 98.4%] |
| IGFBP-7_ng_mL | 78.4 | 94.0% | [83.5%, 98.7%] | 26.0% | [17.7%, 35.7%] |
| sFlt_1_PlGF_ratio | 56.8 | 96.0% | [86.3%, 99.5%] | 95.9% | [89.9%, 98.9%] |
| sFlt_1_PlGF_ratio | 75.0 | 94.0% | [83.5%, 98.7%] | 99.0% | [94.4%, 100.0%] |

Figure 6:
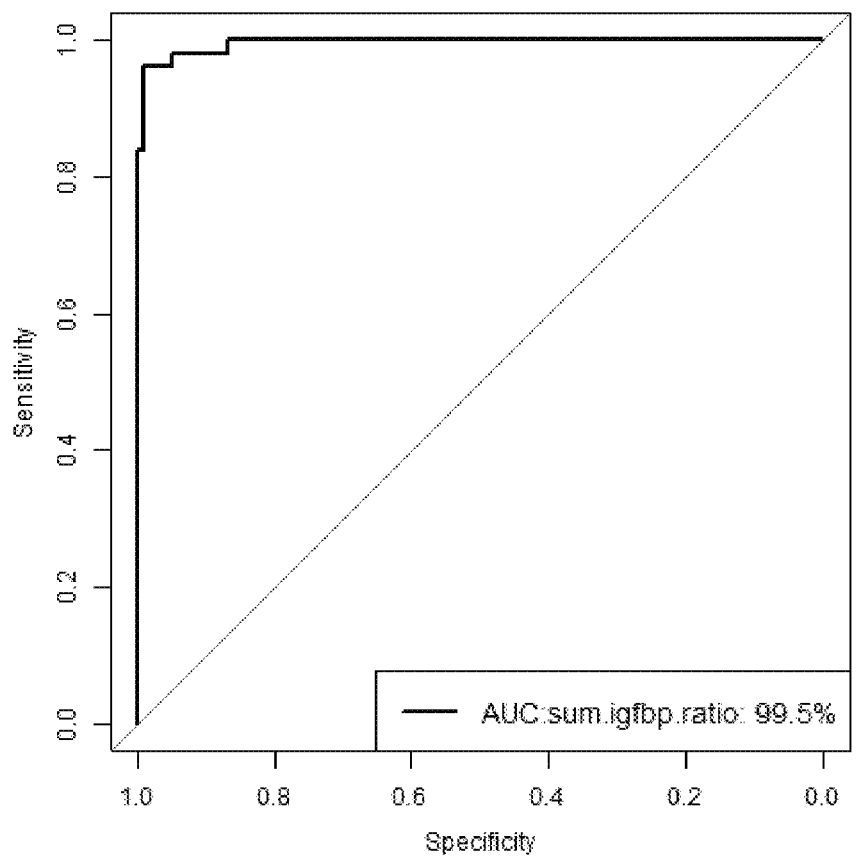
FIG. 6: ROC curve for sum of sFlt-1/PlGF ratio and IGFBP-7 for control group and PE and severe PE cases.

An analysis of the sum of IGFBP-7 and sFlt-1/PlGF is shown in FIG. 6 and Table 3.

TABLE 3

| summary table for ROC curve. Severe PE and PE cases | | | | |
|---|---|---|---|---|
| Threshold | Sens | Sens_CI | Spec | Spec_CI |
| 149.0 | 96.0% | [86.3%, 99.5%] | 95.9% | [89.9%, 98.9%] |
| 167.7 | 94.0% | [83.5%, 98.7%] | 99.0% | [94.4%, 100.0%] |

2. ROC Results for Early PE Cases

Figure 7:
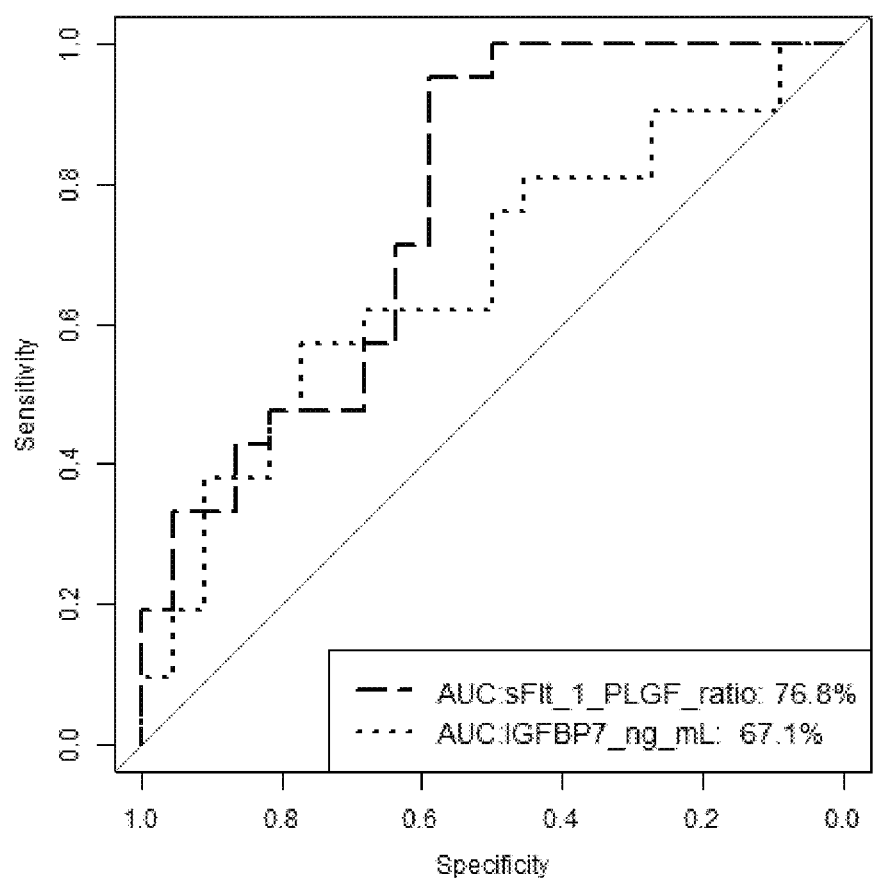
FIG. 7: ROC curve for sFlt-1/PlGF ratio and IGFBP-7 for control group and early PE cases.

An analysis of IGFBP-7 and sFlt-1/PlGF separately is shown in FIG. 7 and Table 4.

TABLE 4

| | summary table for ROC curve. Early PE cases | | | | |
|---|---|---|---|---|---|
| variable | threshold | Sens | Sens_CI | Spec | Spec_CI |
| IGFBP-7_ng_mL | 77.6 | 100.0% | [83.9%, 100.0%] | 9.1% | [1.1%, 29.2%] |
| IGFBP-7_ng_mL | 162.7 | 4.8% | [0.1%, 23.8%] | 100.0% | [84.6%, 100.0%] |
| sFlt_1_PlGF_ratio | 52.3 | 100.0% | [83.9%, 100.0%] | 9.1% | [1.1%, 29.2%] |
| sFlt_1_PlGF_ratio | 1335.1 | 4.8% | [0.1%, 23.8%] | 100.0% | [84.6%, 100.0%] |

Figure 8:
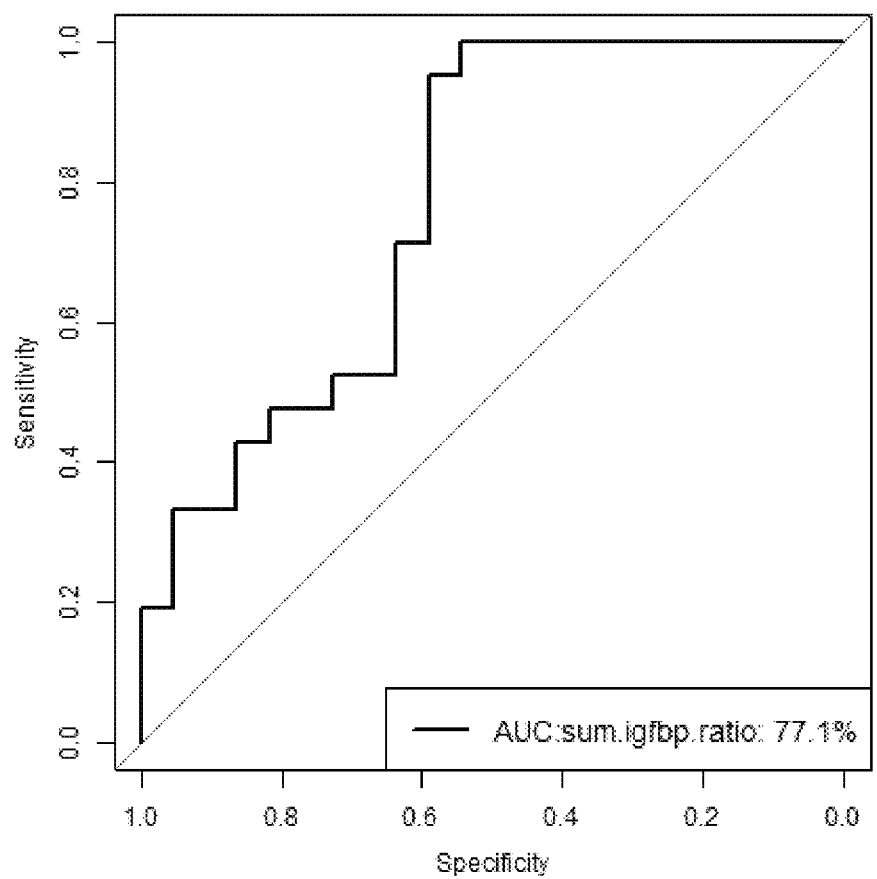
FIG. 8: ROC curve for sum of sFlt-1/PlGF ratio and IGFBP-7 for early PE cases.

An analysis of the sum of IGFBP-7 and sFlt-1/PlGF is shown in FIG. 8 and Table 5.

TABLE 5 summary table for ROC curve. Early PE cases

| Threshold | Sens | Sens_CI | Spec | Spec_CI |
|---|---|---|---|---|
| 146.8 | 100.0% | [83.9%, 100.0%] | 9.1% | [1.1%, 29.2%] |
| 1445.8 | 4.8% | [0.1%, 23.8%] | 100.0% | [84.6%, 100.0%] |

3. ROC Results for Late PE Cases

Figure 9:
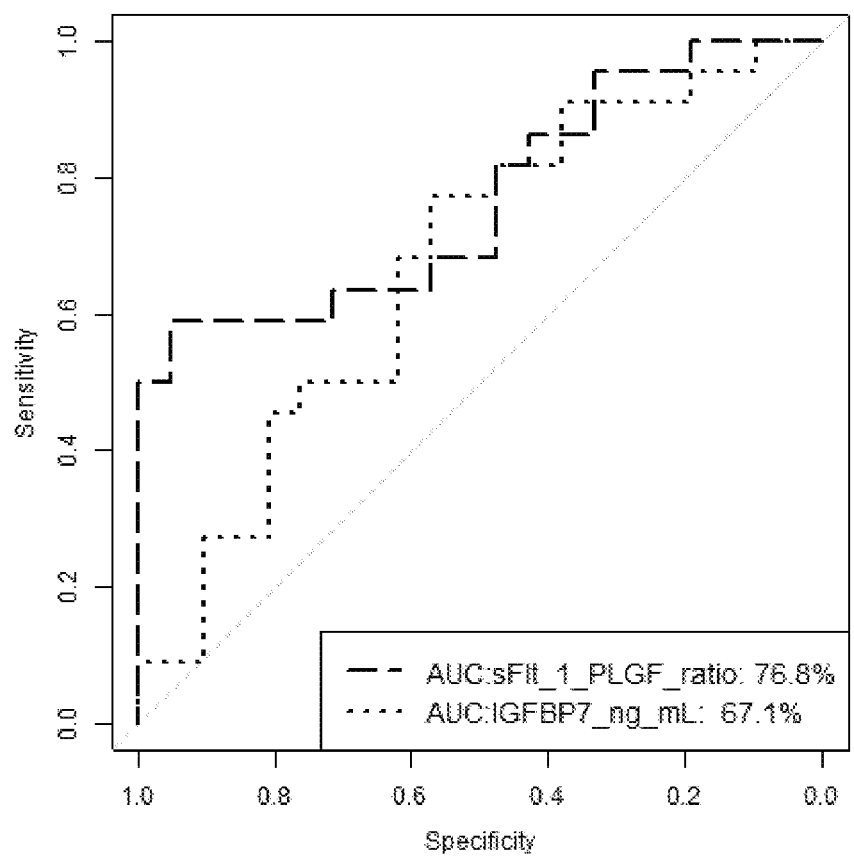
FIG. 9: ROC curve for sFlt-1/PlGF ratio and IGFBP-7 for late PE cases.

An analysis of IGFBP-7 and sFlt-1/PlGF separately is shown in FIG. 9 and Table 6.

TABLE 6 summary table for ROC curve. Late PE cases

| variable | threshold | Sens | Sens_CI | Spec | Spec_CI |
|---|---|---|---|---|---|
| IGFBP-7_ng_mL | 90.3 | 90.9% | [70.8%, 98.9%] | 9.5% | [1.2%, 30.4%] |
| IGFBP-7_ng_mL | 148.5 | 4.5% | [0.1%, 22.8%] | 81.0% | [58.1%, 94.6%] |
| sFlt_1_PlGF_ratio | 142.2 | 40.9% | [20.7%, 63.6%] | 9.5% | [1.2%, 30.4%] |
| sFlt_1_PlGF_ratio | 636.6 | 4.5% | [0.1%, 22.8%] | 66.7% | [43.0%, 85.4%] |

Figure 10:
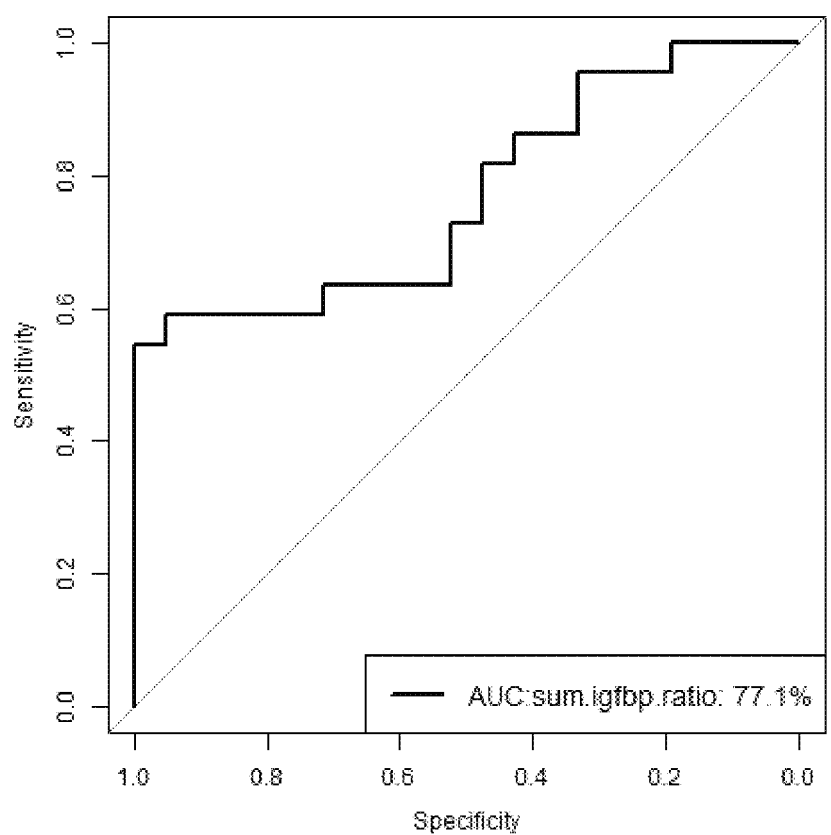
FIG. 10: ROC curve for sum of sFlt-1/PlGF ratio and IGFBP-7 for late PE cases.

An analysis of the sum of IGFBP-7 and sFlt-1/PlGF is shown in FIG. 10 and Table 7.

TABLE 7 summary table for ROC curve (sum). Late PE cases

| Threshold | Sens | Sens_CI | Spec | Spec_CI |
|---|---|---|---|---|
| 262.4 | 40.9% | [20.7%, 63.6%] | 9.5% | [1.2%, 30.4%] |
| 739.5 | 4.5% | [0.1%, 22.8%] | 66.7% | [43.0%, 85.4%] |

The invention claimed is:

1. A method for diagnosing and treating preeclampsia or a preeclampsia-related condition selected from the group consisting of eclampsia, Hemolysis, elevated liver enzymes, low platelet count (HELLP) syndrome and proteinuria in a pregnant subject, said method comprising the steps of
   (a) measuring the amount of IGFBP-7 (Insulin-like Growth Factor Binding Protein 7) polypeptide in a sample from the subject,
   (b) comparing the measured amount of the biomarker to a reference,
   (c) based on the comparison of step (b), identifying the subject as having preeclampsia or a preeclampsia-related condition when the measured amount is increased compared to the reference; and
   (d) administering one or more of corticosteroids, magnesium sulfate and blood pressure reducing agents to the subject identified as having preeclampsia or a preeclampsia-related condition.

2. The method of claim 1, wherein the sample is a body fluid.

3. The method of claim 1, wherein the sample is a blood, serum or plasma sample.

4. The method of claim 1, wherein the subject is a human subject.

5. The method of claim 1, wherein the subject suffers from hypertension.

6. The method of claim 1, further comprising the measurement of the amount of at least one biomarker selected from the group of sFlt-1 (Soluble fms-like tyrosine kinase-1), Endoglin and PlGF (Placental Growth Factor) in a sample from the subject.

7. The method of claim 6, wherein the amounts of
   (i) the biomarkers sFlt-1 and PlGF, or
   (ii) the biomarkers Endoglin and PlGF
   are measured, and wherein a ratio of the amounts of (i) the biomarkers sFlt-1 and PlGF or (ii) the biomarkers Endoglin and PlGF is calculated.

8. A method for monitoring preeclampsia or a preeclampsia-related condition in a pregnant subject suffering from preeclampsia or a preeclampsia-related condition selected from the group consisting of eclampsia, HELLP syndrome and proteinuria, comprising the steps of
   (a) measuring the amount of the polypeptide biomarker IGFBP-7 in a first sample from the subject,
   (b) measuring the amount of the polypeptide biomarker IGFBP-7 in a second sample from the subject,
   (c) comparing the amount of the biomarker in the second sample to the amount of the biomarker in the first sample;
   (d) based on the comparison of step (c), identifying an increase in the severity of preeclampsia or a preeclampsia-related condition in the subject when the amount of IGFBP-7 in the second sample is increased as compared to the amount of IGFBP-7 in the first sample; and
   (e) administering one or more of corticosteroids, magnesium sulfate and blood pressure reducing agents to the subject identified as having an increase in the severity of preeclampsia or a preeclampsia-related condition.

9. The method of claim 1, wherein the at least one agent is a monoclonal antibody.

10. The method of claim 8, wherein the at least one agent is a monoclonal antibody.

11. The method of claim 1, wherein the reference is a pregnant subject or a group of pregnant subjects known not to suffer from preeclampsia or a preeclampsia-related condition.

12. The method of claim 11, wherein the pregnant subject or group of pregnant subjects are at the same stage of gestation as the subject.

13. The method of claim 1, wherein the reference allows for differentiating between a subject suffering from preeclampsia or a preeclampsia-related condition and a subject not suffering from preeclampsia or a preeclampsia-related condition.

* * * * *